(12) United States Patent
Feler

(10) Patent No.: US 6,236,892 B1
(45) Date of Patent: May 22, 2001

(54) SPINAL CORD STIMULATION LEAD

(76) Inventor: Claudio A. Feler, 350 Sweetbriar Rd., Memphis, TN (US) 38120

(*) Notice: Subject to any disclaimer, the term of this patent is extended or adjusted under 35 U.S.C. 154(b) by 0 days.

(21) Appl. No.: 09/414,410

(22) Filed: Oct. 7, 1999

(51) Int. Cl.$^7$ .................................................. A61N 1/05
(52) U.S. Cl. ........................................................ 607/117
(58) Field of Search ............................. 607/46, 117, 116, 607/115

(56) References Cited

U.S. PATENT DOCUMENTS

| | | | |
|---|---|---|---|
| 3,724,467 | 4/1973 | Avery et al. | 128/418 |
| 3,822,708 | 7/1974 | Zilber | 128/419 R |
| 5,417,719 | 5/1995 | Hull et al. | 607/46 |
| 5,643,330 | 7/1997 | Holsheimer et al. | 607/46 |
| 5,735,885 | 4/1998 | Howard, III et al. | 607/55 |

FOREIGN PATENT DOCUMENTS

| | | |
|---|---|---|
| 195 25 570 A 1 | 1/1996 | (DE) . |
| 197 58 114 A 1 | 7/1999 | (DE) . |
| 643158 | 1/1979 | (SU) . |

OTHER PUBLICATIONS

Advanced Neuromodulation Systems; *Lamitrode SCS Leads*; Integrating Performance and Stability, Mar. 1997.

*Primary Examiner*—Scott M. Getzow
(74) *Attorney, Agent, or Firm*—Sidley & Austin

(57) ABSTRACT

The present invention relates to an epidural laminotomy stimulation lead having at least first and second electrode arrays. To enable a greater effective stimulation length, the longitudinal spacing between the various electrode arrays is greater than a smallest regular longitudinal spacing between electrodes of the electrode arrays.

13 Claims, 1 Drawing Sheet

SPINAL CORD STIMULATION LEAD

FIELD OF THE INVENTION

The present invention relates to an epidural stimulation lead, and in particular, to an epidural stimulation laminotomy lead and method of using the same.

BACKGROUND OF THE INVENTION

Application of specific electrical fields to spinal nerve roots, spinal cord, and other nerve bundles for the purpose of chronic pain control has been actively practiced since the 1960s. While a precise understanding of the interaction between the applied electrical energy and the nervous tissue is not fully appreciated, it is known that application of an electrical field to spinal nervous tissue (i.e., spinal nerve roots and spinal cord bundles) can effectively mask certain types of pain transmitted from regions of the body associated with the stimulated tissue. More specifically, applying particularized electrical energy to the spinal cord associated with regions of the body afflicted with chronic pain can induce paresthesia, or a subjective sensation of numbness or tingling, in the afflicted bodily regions. This paresthesia can effectively mask the transmission of non-acute pain sensations to the brain.

It is known that each exterior region, or each dermatome, of the human body is associated with a particular spinal nerve root at a longitudinal spinal position. Thus, the head and neck regions are associated with C2–C8, the back is from C2–S3, the central diaphragm is between C3 and C5, the upper extremities are between C5 and T1, the thoracic wall is between T1 and T11, the peripheral diaphragm is between T6 and T11, the abdominal wall is associated with T6–L1, lower extremities are located from L2 to S2, and the perineum from L4 to S4. By example, to address chronic pain sensations that commonly focus on the lower back and lower extremities, a specific energy field can usually be applied to a region between bony level T8 and T10. As should be understood, successful pain management and the avoidance of stimulation in unafflicted regions necessarily requires the applied electric field to be properly positioned longitudinally along the dorsal column.

Positioning of an applied electrical field relative to a physiological midline is equally important. Nerve fibers extend between the brain and a nerve root along the same side of the dorsal column as the peripheral areas the fibers represent. Pain that is concentrated on only one side of the body is "unilateral" in nature. To address unilateral pain, electrical energy is applied to neural structures on the side of a dorsal column that directly corresponds to a side of the body subject to pain. Pain that is present on both sides of a patient is "bilateral." Accordingly, bilateral pain is addressed through either an application of electrical energy along a patient's physiological midline or an application of electrical energy that transverses the physiological midline.

Pain managing electrical energy is commonly delivered through electrodes positioned external to the dura layer surrounding the spinal cord. The electrodes are carried by two primary vehicles: a percutaneous catheter and a laminotomy lead.

Percutaneous catheters, or percutaneous leads, commonly have three or more, equally-spaced electrodes, which are positioned above the dura layer through the use of a Touhy-like needle. For insertion, the Touhy-like needle is passed through the skin, between desired vertebrae, to open above the dura layer.

For unilateral pain, percutaneous leads are positioned on a side of a dorsal column corresponding to the "afflicted" side of the body, as discussed above, and for bilateral pain, a single percutaneous lead is positioned along the patient midline (or two or more leads are positioned on each side of the midline).

Laminotomy leads have a paddle configuration and typically possess a plurality of electrodes (for example, two, four, eight, or sixteen) arranged in one or more independent columns. For each column having more than one electrode, the electrodes for such columns are equally spaced. An example of a sixteen-electrode laminotomy lead is shown in FIG. 1.

Implanted laminotomy leads are commonly transversely centered over the physiological midline of a patient. In such position, multiple columns of electrodes are well suited to address both unilateral and bilateral pain, where electrical energy may be administered using either column independently (on either side of the midline) or administered using both columns to create an electric field which traverses the midline. A multi-column laminotomy lead enables reliable positioning of a plurality of electrodes, and in particular, a plurality of electrode columns that do not readily deviate from an initial implantation position.

Laminotomy leads require a surgical procedure for implantation. The surgical procedure, or partial laminectomy, requires the resection and removal of certain vertebral tissue to allow both access to the dura and proper positioning of a laminotomy lead. The laminotomy lead offers a more stable platform, which is further capable of being sutured in place, that tends to migrate less in the operating environment of the human body.

Percutaneous leads require a less-invasive implantation method and, with a plurality of leads, provide a user the ability to create almost any electrode array. While likely more stable during use, laminotomy leads do not offer an opportunity for electrode array variance due to the fixed nature of their electrode arrays. It is common practice that the electrodes of both percutaneous leads and laminotomy leads are equally spaced in a longitudinal direction.

A maximum number of electrodes for a lead, whether percutaneous or laminotomy, is dictated by known stimulation systems. Current stimulation systems (not shown) enable 4-stimulation channels, 8-stimulation channels, or 16-stimulation channels, where each "channel" represents a controllable electrical output. Thus, conventional stimulation leads include at least two but no more than 16 electrodes, wherein each electrode is respectively coupled to a single stimulation system output. Given that the number of electrodes of conventional stimulation leads are determined by a coupled stimulation system (as opposed to a patient's physical condition), the provision of equal, longitudinal spacing between such electrodes results in limited effective stimulation lengths.

To this end, a significant number of spinal cord stimulation cases for the management of pain involve a combination of lower back and leg pain. To address these particular regions, it is desirous to target electrical energy between the pedicles of T8 and T9 (lower back) and T10–L1 (depending on the particular leg segment). Due to the distance between these sites and the complex nature of such pain, it is necessary to use multiple leads, whether of a percutaneous form and/or a laminotomy form.

Consequently, a need exists for a laminotomy lead that, within the arbitrary boundaries of conventional stimulation systems, can provide a greater effective stimulation length to enable delivery of electrical energy over a greater range of spinal nervous tissue. To this end, a further need exists for a laminotomy lead that is capable of addressing complex pain commonly affecting the lower back and legs.

SUMMARY OF THE INVENTION

The present invention is drawn to a stimulation lead having a plurality of terminals, a plurality of electrodes carried by a body, and a plurality of conductors, as a conductor electrically couples one terminal with a respective electrode. The plurality of electrodes form a first electrode group and a second electrode group, and the first electrode group is longitudinally spaced apart from the second electrode group by a first distance. The first electrode group includes at least three electrodes arranged in a longitudinally-oriented column, and the at least three electrodes are individually separated by a second distance, such second distance being less than the first distance. The second electrode group includes at least three electrodes arranged in a longitudinally-oriented column, and the at least three electrodes are individually separated by a third distance, such third distance being at least equal to the second distance.

As another aspect of the present invention, a stimulation lead is disclosed having a plurality of terminals, a plurality of electrodes carried by a body, and a plurality of conductors. A portion of the plurality of electrodes is arranged in three longitudinal columns. One such column, positioned between a first electrode column and a third electrode column, has at least two independent electrodes that are electrically coupled to respective terminals via individual conductors. Each of the at least two independent electrodes have a single conductive surface. The first column includes one electrode electrically coupled to a terminal of the plurality of terminals via an individual conductor of the plurality of conductors, such electrode has a plurality of conductive surfaces.

An object of the present invention is to provide a laminotomy lead having a significant effective stimulation length.

Another object of the present invention is to provide, for at least one application, a single laminotomy lead capable of addressing complex pain afflicting, in common, a patient's lower back and legs.

Other objects and advantages of the present invention will be apparent to those of ordinary skill in the art having reference to the following specification together with the drawings.

DETAILED DESCRIPTION OF THE PREFERRED EMBODIMENTS

Various embodiments, including preferred embodiments, will now be described in detail below with reference to the drawings.

Figure 1:
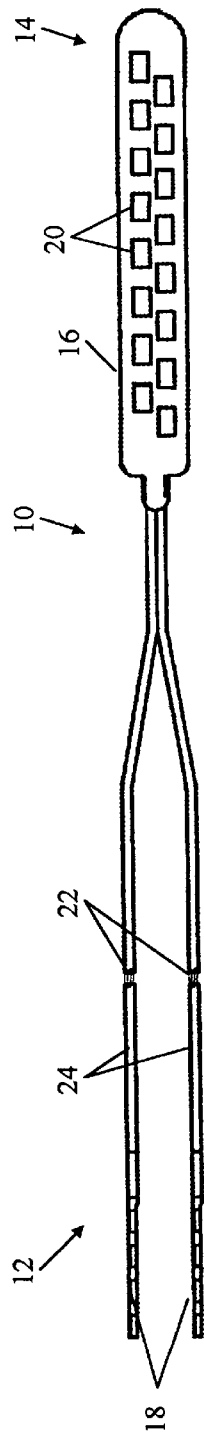
FIG. 1 is a plan view of a conventional laminotomy spinal cord stimulation lead.

In reference to FIG. 1, the illustrated laminotomy lead 10 includes a proximal end 12 and a distal end 14. The proximal end 12 includes a plurality of electrically conductive terminals 18, and the distal end 14 includes a plurality of electrically conductive electrodes 20 arranged within a flat, thin paddle-like structure 16. Typically, each terminal 18 is electrically connected to a single electrode 20 via a conductor 22; however, a terminal 18 can be connected to two or more electrodes 20.

Terminals 18 and electrodes 20 are preferably formed of a non-corrosive, highly conductive material. Examples of such material include stainless steel, MP35N, platinum, and platinum alloys. In a preferred embodiment, terminals 18 and electrodes 20 are formed of a platinum-iridium alloy.

Figure 3:
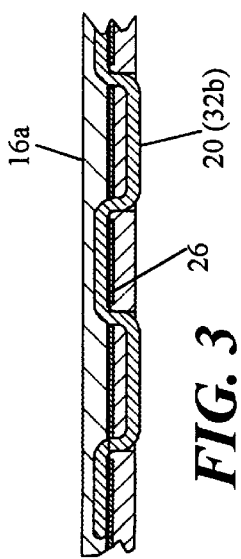
FIG. 3 is a partially sectional view of the stimulation lead of FIG. 2, taken along line III—III.

The sheaths 24 and the paddle structure 16 are formed from a medical grade, substantially inert material, for example, polyurethane, silicone, or the like. Importantly, such material must be non-reactive to the environment of the human body, provide a flexible and durable (i.e., fatigue resistant) exterior structure for the components of lead 10, and insulate adjacent terminals 18 and/or electrodes 20. Of note, additional structure 26 (e.g., a nylon mesh, a fiberglass substrate) can be internalized within the paddle structure 16 to increase its overall rigidity (FIG. 3) and/or to cause the paddle structure 16 to assume a prescribed cross-sectional form (e.g., a prescribed arc along a transverse direction of the paddle structure 16)(not shown).

The conductors 22 are carried in sheaths 24. In the illustrated example, each sheath 24 carries eight (8) conductors 22. Given the number of conductors 22 that are typically carried within each sheath 24, the cross-sectional area of each conductor 20 is restricted. As but one example, for a sheath 24 in accordance with the present invention, having an outer diameter of approximately 0.055 inches, each conductor 22 would be approximately 0.0065 inches in diameter.

Each conductor 22 is formed of a conductive material that exhibits the desired mechanical properties of low resistance, corrosion resistance, flexibility, and strength. While conventional stranded bundles of stainless steel, MP35N, platinum, platinum-iridium alloy, drawn-brazed silver (DBS) or the like can be used, a preferred embodiment of the present invention uses conductors 22 formed of multi-strands of drawn-filled tubes (DFT) . Each strand is formed of a low resistance material and is encased in a high strength material (preferably, metal). A selected number of "sub-strands" are wound and coated with an insulative material. With regard to the operating environment of the present invention, such insulative material protects the individual conductors 22 if its respective sheath 24 was breached during use. Wire formed of multi-strands of drawn-filled tubes to form conductors 22, as discussed here, is available from Temp-Flex Cable, Inc. (City, State).

In addition to providing the requisite strength, flexibility, and resistance to fatigue, conductors 22 formed of multi-strands of drawn-filled tubes, in accordance with the above description, provide a low resistance alternative to other conventional materials. Specifically, a stranded wire, or even a coiled wire, of approximately 60 cm and formed of MP35N or stainless steel or the like would have a measured resistance in excess of 30 ohms. In contrast, for the same length, a wire formed of multi-strands of drawn-filled tubes could have a resistance less than 4 ohms. Accordingly, in a preferred embodiment, each conductor 22, having a length equal to or less than 60 cm, has a resistance of less than 25 ohms. In a more preferred embodiment, each conductor 20, having a length equal to or less than 60 cm, has a resistance equal to or less than 10 ohms. In a most preferred embodiment, each conductor 20, having a length equal to or less than 60 cm, has a resistance of less than 4 ohms.

While a number of material and construction options have been discussed above, it should be noted that neither the materials selected nor a construction methodology is critical to the present invention.

The following discussion is directed to a number of examples illustrated in FIGS. 2–5. While the examples set forth a variety of variations of the present invention, it may be readily appreciated that the present invention could take any of a variety of forms and include any number of electrodes. Importantly, however, the present invention is characterized by a first electrode array longitudinally displaced and separated from a second electrode array to provide a greater effective stimulation length but still enable effective delivery of electrical energy. To clarify such structure, the following examples are provided.

Figure 2:
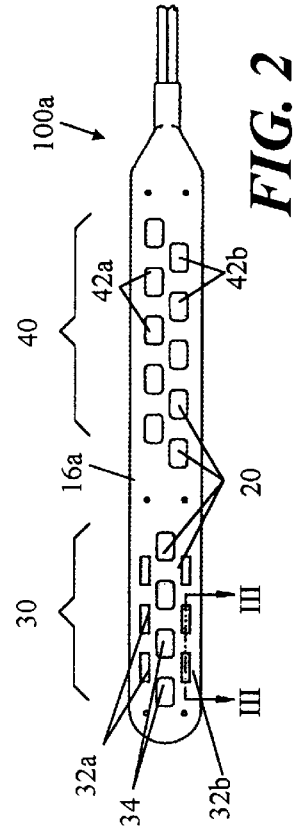
FIG. 2 is a plan view of a first embodiment of a laminotomy spinal cord stimulation lead in accordance with the present invention.

FIG. 2 illustrates a laminotomy lead 100a in accordance with a first embodiment of the present invention. The paddle structure 16a includes a plurality of electrodes 20, which are divided into two groups: a distal group 30 and a proximal group 40.

The proximal group 40 includes ten (10) electrodes 20 (42a, 42b) arranged in two columns, each column having five electrodes. While it has long been recognized that a "staggered" configuration of longitudinally arranged electrodes is desirable (i.e., primarily for space consideration), the electrodes of group 40 may be transversely aligned.

The distal group 30 of electrodes 32 and 34 is arranged in three columns, thus enabling formation of a transverse tripole electric field. While inconclusive, it appears that a transverse tripole field provides some advantage in addressing lower back pain. Consequently, it is intended that distal group 30 would operatively be positioned relative to applicable nervous tissue to effect management of certain back pain.

In reference to FIG. 2, it appears that laminotomy lead 100a includes twenty (20) electrodes 20. While future stimulation systems may include an unlimited number of controllable, electrical outputs that would allow each of the electrodes 20 to be associated with an independent output, laminotomy lead 100a is constructed to operate within the artificial boundaries of current stimulation systems. Specifically, the electrodes 32a and the electrodes 32b are respectively formed from unitary conductive structures (see FIG. 3). Consequently, the electrodes 32a (and the electrodes 32b) are coupled to a single conductor 22 and a corresponding single electrical output of an operatively connected stimulation system.

The distal group 30 may be operatively configured to focus delivered electrical energy and avoid the undesirable stimulation of collateral nervous tissue. Specifically, utilizing electrodes 32a and 32b as anodes, where one or more of electrodes 34 assume a negative polarity, an electric field may be established that minimizes a respective quantity of transverse electrical energy delivered in regard to a transverse dimension of the laminotomy lead 100a.

In a preferred embodiment, the electrodes 20 are approximately 4 mm in length, wherein the electrodes 34, 42a, and 42b are approximately 2.5 mm in width, and the electrodes 32a and 32b are approximately 1.2 mm in width. The center-to-center longitudinal spacing of the electrodes 32a, the electrodes 32b, and the electrodes 34 is approximately 5–7 mm. The center-to-center longitudinal spacing of the electrodes 42a and the electrodes 42b is approximately 7 mm.

It should be noted, however, that the above dimensions are not critical to the present invention; but rather, such dimensions should better relate to the nature of the pain/motor condition to be managed. The dimensions set forth here have been proven to facilitate delivery of the necessary electrical energy with respect to spinal nervous tissue. As should be noted, however, as the longitudinal spacing between adjacent electrodes increases, the ability of a user to refine the delivery of focused electrical energy decreases.

The distance between a distal-most electrode 42b of the proximal group 40 and a proximal-most electrode 34 of the distal group 30 is approximately 9.5 mm, or approximately 3 to 10 times the longitudinal spacing between the various electrodes of the first group 30 and the second group 40. More generally, the longitudinal spacing between the various electrodes of the first group 30 and the second group 40 is most preferably greater than the smallest regular longitudinal spacing of the electrodes 20 for either the distal group 30 and the proximal group 40. Accordingly, but for the absence of electrodes in that space separating the first group 30 from the second group 40, the laminotomy lead 100a has an effective stimulation length of approximately 70 mm.

The laminotomy lead 100a enables an increased effective stimulation length with a maximum number of controllable electrodes 20 (i.e., given the operative specifications of a coupled stimulation system). Moreover, each of the electrode groups, whether the distal group 30 or the proximal group 40, include a plurality of electrodes 20, which enable a plurality of possible electrode combinations, both locally within the respective groups 30 and 40 and globally across groups 30 and 40. In a most preferred embodiment, at least one column of electrodes 20 in each group 30, 40 has at least three electrically independent electrodes 20.

Figure 4:
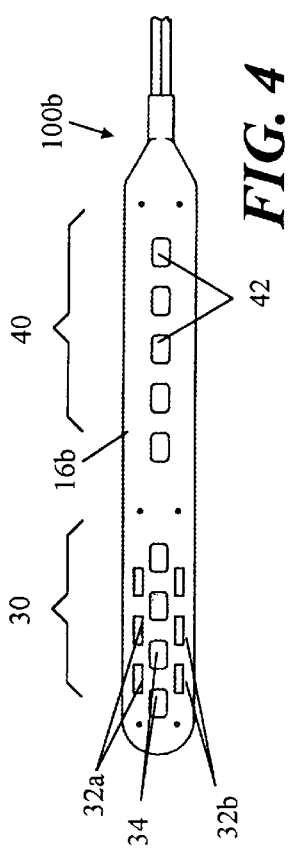
FIG. 4 is a plan view of a second embodiment of a laminotomy spinal cord stimulation lead in accordance with the present invention.

FIG. 4 illustrates a laminotomy lead 100b in accordance with a second embodiment of the present invention. As the first group 30 is identical to that of the laminotomy lead 100a of the first embodiment, a further description of this electrode array will not be provided here.

The second group 40 includes a single column of electrodes 42. While in the illustrated example the column includes five independent electrodes 42, such column could include any number of electrodes 42, subject, of course, to a connected stimulation system. Similar to the structure of laminotomy lead 100a, the laminotomy lead 100b has an effective stimulation length of approximately 70 mm.

Figure 5:
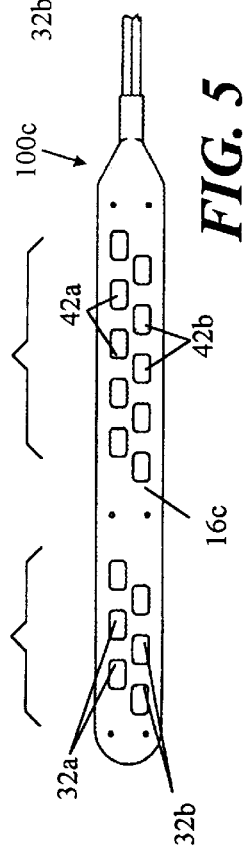
FIG. 5 is a plan view of a third embodiment of a laminotomy spinal cord stimulation lead in accordance with the present invention.

FIG. 5 illustrates a laminotomy lead 100c in accordance with a third embodiment of the present invention. As the second group 40 is identical to that of the laminotomy lead 100a of the first embodiment, a further description of this electrode array will not be provided here.

The first group 40 includes two columns of electrodes 20 (32a, 32b), wherein each column includes three electrodes 20.

While the invention has been described herein relative to a number of particularized embodiments, it is understood that modifications of, and alternatives to, these embodiments, such modifications and alternatives realizing the advantages and benefits of this invention, will be apparent those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A stimulation lead comprising:
    a body;
    a plurality of terminals;
    a plurality of electrodes, carried by the body; and
    a plurality of conductors, wherein a conductor electrically couples one terminal with a respective electrode,
    wherein the plurality of electrodes form a first electrode group and a second electrode group, and the first electrode group is longitudinally spaced apart from the second electrode group by a first distance,
    wherein the first electrode group includes at least three electrodes arranged in a longitudinally-oriented column, and the at least three electrodes are individually separated by a second distance,
    wherein the second electrode group includes at least three electrodes arranged in a longitudinally-oriented column, and the at least three electrodes are individually separated by a third distance, and
    wherein the first distance is greater than the second distance, and the third distance is at least equal to the second distance.

2. A stimulation lead in accordance with claim 1, wherein the second distance and the third distance are approximately equal.

3. A stimulation lead in accordance with claim 1, wherein the second distance is approximately 2 mm.

4. A stimulation lead in accordance with claim 1, wherein the first distance is at least three times the second distance.

5. A stimulation lead in accordance with claim 1, wherein the second electrode group includes a plurality of electrodes arranged in at least two longitudinal columns, and each column of the second electrode group includes at least two electrodes.

6. A stimulation lead comprising:
    a body having a first surface;
    a plurality of terminals;
    a plurality of electrodes, carried by the body; and
    a plurality of conductors, wherein a conductor electrically couples one terminal with a respective electrode,
    wherein the plurality of electrodes consists of a first electrode group and a second electrode group, and the first electrode group is longitudinally spaced apart from the second electrode group by a first distance,
    wherein the first electrode group includes at least two electrodes arranged in a longitudinally-oriented column, and the at least two electrodes are individually separated by a second distance,
    wherein the second electrode group includes a plurality of electrodes arranged in at least two longitudinally-oriented columns, and
    wherein the first distance is greater than the second distance.

7. A stimulation lead in accordance with claim 6, wherein the first distance is at least three times the second distance.

8. A stimulation lead in accordance with claim 6, wherein the second distance is approximately 2 mm.

9. A stimulation lead in accordance with claim 6, wherein the plurality of electrodes of the second group is arranged in three longitudinal columns, one such column, positioned between a first electrode column and a third electrode column, has at least two independent electrodes that are electrically coupled to respective terminals of the plurality of terminals via individual conductors of the plurality of conductors, each of the at least two independent electrodes having a single conductive surface relative to the first surface of the body,
    wherein the first column includes one electrode electrically coupled to a terminal of the plurality of terminals via an individual conductor of the plurality of conductors, such one electrode having a plurality of conductive surfaces relative to the first surface of the body, and
    wherein the third column includes one electrode electrically coupled to a terminal of the plurality of terminals via an individual conductor of the plurality of conductors, such one electrode having a plurality of conductive surfaces relative to the first surface of the body.

10. A stimulation lead comprising:
    a body;
    a plurality of terminals;
    a plurality of electrodes, carried by the body; and
    a plurality of conductors, wherein a conductor electrically couples one terminal with a respective electrode,
    wherein the plurality of electrodes consists of a first electrode group and a second electrode group, and the first electrode group is longitudinally spaced apart from the second electrode group by a first distance,
    wherein the first electrode group includes at least three electrodes arranged in a longitudinally-oriented column, and the at least three electrodes are individually separated by a second distance,
    wherein the second electrode group includes a plurality of electrodes arranged in three longitudinally-oriented columns, and at least one of such columns of the second electrode group includes at least three electrodes, and
    wherein the first distance is greater than the second distance.

11. A stimulation lead comprising:
    a body having a first surface;
    a plurality of terminals;
    a plurality of electrodes carried by the body; and
    a plurality of conductors,
    wherein at least a portion of the plurality of electrodes is arranged in three longitudinal columns, one such column, positioned between a first electrode column and a third electrode column, has at least two independent electrodes that are electrically coupled to respective terminals of the plurality of terminals via individual conductors of the plurality of conductors, each of the at least two independent electrodes having a single conductive surface relative to the first surface of the body,
    wherein the first column includes one electrode electrically coupled to a terminal of the plurality of terminals via an individual conductor of the plurality of conductors, such one electrode having a plurality of conductive surfaces relative to the first surface of the body, and
    wherein the third column includes one electrode electrically coupled to a terminal of the plurality of terminals via an individual conductor of the plurality of conductors, such one electrode having a plurality of conductive surfaces relative to the first surface of the body.

12. A stimulation lead in accordance with claim 11, wherein the portion of electrodes is a first electrode group and a remaining portion of the plurality of electrodes forms a second electrode group, the first electrode group being longitudinally spaced apart from the second electrode group by a first distance, wherein the second electrode group includes at least three electrodes arranged in a longitudinally-oriented column, and the at least three electrodes are individually separated by a second distance, and wherein the first distance is greater than the second distance.

13. A stimulation lead in accordance with claim 12, wherein the second distance is approximately 2 mm.

\* \* \* \* \*